United States Patent
Choi et al.

(10) Patent No.: US 10,570,429 B2
(45) Date of Patent: Feb. 25, 2020

(54) O-SUCCINYLHOMOSERINE PRODUCING MICROORGANISM AND METHOD FOR PRODUCING O-SUCCINYLHOMOSERINE USING SAME

(71) Applicant: CJ CHEILJEDANG CORPORATION, Seoul (KR)

(72) Inventors: Su Jin Choi, Daegu (KR); Kuk Ki Hong, Goyang-si (KR); Young Lyeol Yang, Seoul (KR); Min Sun Kang, Seoul (KR); Hye Min Park, Gimhae-si (KR); Gyuhyeon Song, Seoul (KR); Jong Hyun Yoon, Seoul (KR)

(73) Assignee: CJ CHEILJEDANG CORPORATION, Gyeonggi-Do (KR)

( * ) Notice: Subject to any disclaimer, the term of this patent is extended or adjusted under 35 U.S.C. 154(b) by 0 days.

(21) Appl. No.: 15/303,196

(22) PCT Filed: Jan. 22, 2015

(86) PCT No.: PCT/KR2015/000677
§ 371 (c)(1),
(2) Date: Oct. 10, 2016

(87) PCT Pub. No.: WO2015/156484
PCT Pub. Date: Oct. 15, 2015

(65) Prior Publication Data
US 2017/0101656 A1 Apr. 13, 2017

(30) Foreign Application Priority Data
Apr. 10, 2014 (KR) .................. 10-2014-0043187

(51) Int. Cl.
*C12P 13/06* (2006.01)
*C12N 15/70* (2006.01)
*C12N 15/52* (2006.01)

(52) U.S. Cl.
CPC .............. *C12P 13/06* (2013.01); *C12N 15/52* (2013.01); *C12N 15/70* (2013.01)

(58) Field of Classification Search
CPC .......... C12N 15/70; C12N 15/52; C12P 13/06
See application file for complete search history.

(56) References Cited

U.S. PATENT DOCUMENTS 7,851,180 B2 * 12/2010 Shin ................. C12P 13/06
435/252.1
8,465,952 B2 6/2013 Kim et al.
8,741,623 B2 6/2014 Zelder et al.
9,169,502 B2 10/2015 Wittmann et al.
2009/0029425 A1 1/2009 Zelder et al.

FOREIGN PATENT DOCUMENTS

| EP | 1390504 B1 | 4/2011 |
|----|------------|--------|
| KR | 1020080113225 | 12/2008 |
| KR | 1020090005099 | 1/2009 |
| KR | 1020090106365 A | 10/2009 |
| KR | 101136248 | 4/2012 |
| KR | 1020120108040 | 10/2012 |
| RU | 2355759 C1 | 8/2007 |
| RU | 2307169 C1 | 9/2007 |
| WO | 03008600 A2 | 1/2003 |
| WO | 2008013432 A1 | 1/2008 |
| WO | 2013105807 A2 | 7/2013 |

OTHER PUBLICATIONS

Zhou et al., Cell Mol Life Sci 63(19-20):2260-2290, 2006.*
Kozak, M., Gene 234:187-208, 1999.*
Branch, A., TIBS 23:45-50, 1998.*
Zhao et al., Applied Microbiology and Biotechnology 64:91-98, 2004.*
Schneider et al., Journal of Bacteriology 180(6):4278-4286, 1998.*
International Search Report—PCT/KR2015/000677 dated Apr. 15, 2015.
Written Opinion—PCT/KR2015/000677 dated Apr. 15, 2015.
Abhishek Murarka et al., Metabolic flux analysis of wild-type *Escherichia coli* and mutants deficient in pyruvate-dissimilating enzymes during the fermentative metabolism of glucuronate, 2010, pp. 1860-1872, 156, Microbiology.
Cecile Nicolas et al., Response of the central metabolism of *Escherichia coli* to modified expression of the gene encoding the glucose-6-phosphate dehydrogenase, 2007, pp. 3771-3776, 581, FEBS Letters.
Jiao Zhao et al., Effect of zwf gene knockout on the metabolism of *Escherichia coli* grown on glucose or acetate, 2004, pp. 164-174, 6, Metabolic Engineering, Elsevier.
Yu Matsuoka et al., Metabolic regulation of *Escherichia coli* cultivated under anaerobic and aerobic conditions in response to the specific pathway gene knockouts, 2013, pp. 455-468, 4, Advances in Bioscience and Biotechnology.
Japanese Office Action dated Jul. 11, 2017.
Extended European Search Report for Application No. 15776244.4 dated Jul. 24, 2017.
Russian Office Action for application No. 2016144104 dated Dec. 6, 2017.
Russian meeting minutes for application No. 2016144104 dated Sep. 25, 2018.

* cited by examiner

*Primary Examiner* — Delia M Ramirez
(74) *Attorney, Agent, or Firm* — Cantor Colburn LLP

(57) ABSTRACT

Provided are a microorganism of the genus *Escherichia* for producing O-succinylhomoserine and a method for producing O-succinylhomoserine using the same.

5 Claims, No Drawings
Specification includes a Sequence Listing.

O-SUCCINYLHOMOSERINE PRODUCING MICROORGANISM AND METHOD FOR PRODUCING O-SUCCINYLHOMOSERINE USING SAME

TECHNICAL FIELD

The present disclosure relates to an O-succinylhomoserine-producing microorganism and a method of producing O-succinylhomoserine using the same.

BACKGROUND ART

O-succinylhomoserine is produced by binding of homoserine and a succinyl group of succinyl-CoA in a biosynthetic pathway. Therefore, in the development of a strain producing O-succinylhomoserine with a high yield, production of homoserine and succinyl CoA is important. Of them, succinyl CoA is produced in the TCA cycle, and thus enhancement of the TCA cycle is required for the production of high concentration of succinyl CoA.

Pentose phosphate pathway (PPP) is well known as a major source of NADPH, and biosynthetic pathways of amino acids require a cofactor NADPH. Therefore, to enhance pentose phosphate pathway in the development of amino acid-producing strains, zwf gene encoding glucose 6-phosphate-1-dehydrogenase involved in a first step of the pathway is generally enhanced, and these strains are disclosed in Korean Patent Publication NOs. 2008-0036608 and 2006-0129352.

When expression of zwf gene or activity of an enzyme encoded thereby is attenuated, pentose phosphate pathway is attenuated, leading to a lack of NADPH supply. In this case, NADPH can be partly replenished by overexpression of isocitrate dehydrogenase (icd) and malate dehydrogenase (mae) of the TCA cycle (Appl Microbiol Biotechnol. 2004 64(1); 91-8, Metab Eng. 2004 6(2); 164-74, FEBS Letters 581 2007 3771-6).

The present inventors have studied to develop a strain capable of producing O-succinylhomoserine with high yield and high efficiency, and they developed a strain, in which zwf gene is attenuated and deleted, for the purpose of producing high concentration of succinyl-CoA as a precursor of O-succinylhomoserine in *E. coli* having O-succinylhomoserine productivity. As a result of culturing, the present inventors found that O-succinylhomoserine concentration was increased, thereby completing the present disclosure.

DETAILED DESCRIPTION OF THE INVENTION

Technical Problem

An object of the present disclosure is to provide an O-succinylhomoserine-producing microorganism.

Another object of the present disclosure is to provide a method of producing O-succinylhomoserine, the method including the step of culturing the O-succinylhomoserine-producing microorganism.

Technical Solution

In an aspect, the present disclosure provides an O-succinylhomoserine-producing microorganism.

In a specific embodiment of the present disclosure, the O-succinylhomoserine-producing microorganism may be a microorganism of the genus *Escherichia* for producing O-succinylhomoserine, in which a glucose 6-phosphate-1-dehydrogenase activity is attenuated or eliminated, compared to its endogenous activity.

The term "O-succinylhomoserine-producing microorganism", as used herein, refers to a prokaryotic or eukaryotic microorganism capable of producing O-succinylhomoserine in an organism and accumulating O-succinylhomoserine. For example, the O-succinylhomoserine-producing microorganism may be a microorganism belonging to genus *Escherichia*, genus *Erwinia*, genus *Serratia*, genus *Providencia*, genus *Corynebacteria*, genus *Pseudomonas*, genus *Leptospira*, genus *Salmonella*, genus *Brevibacteria*, genus *Hyphomonas*, genus *Chromobacterium*, genus *Norcardia*, or fungi or yeast. The O-succinylhomoserine-producing microorganism may be specifically a microorganism belonging to genus *Escherichia*, and more specifically, *Escherichia coli* (*E. coli*).

Glucose 6-phosphate-1-dehydrogenase acts in the pentose phosphate pathway which is a metabolic pathway providing a reducing power for cells by maintaining NADPH levels. This enzyme catalyzes oxidation of glucose 6-phosphate to 6-phosphogluconolactone by reducing NADP to NADPH in a first step of the pentose phosphate pathway. A gene encoding this enzyme is commonly called zwf. Attenuation or elimination of this enzyme leads to the flow through the TCA cycle, resulting in enhancement of the TCA cycle.

The glucose 6-phosphate-1-dehydrogenase may have an amino acid sequence of SEQ ID NO: 23. Further, the glucose 6-phosphate-1-dehydrogenase may have an amino acid sequence having 80% or higher, 90% or higher, or 95% % or higher homology with SEQ ID NO: 23.

The term "homology", as used herein in relation to the sequence, refers to a degree of matching with a given amino acid sequence or base sequence, and the homology may be expressed as a percentage. In the present disclosure, a homology sequence having an activity which is identical or similar to the given amino acid sequence or base sequence is expressed as "% homology". For example, the amino acid sequence having 80% or higher, 90% or higher, or 95% % or higher homology with SEQ ID NO: 23 represents a sequence having the activity of glucose 6-phosphate-1-dehydrogenase.

The term "endogenous" enzyme and activity, as used herein, refer to a native enzyme naturally present in a microorganism or a cell and an activity thereof, and in other words, refer to an enzyme and an activity thereof before modification of the corresponding enzyme and activity thereof.

In a specific embodiment of the present disclosure, the microorganism may be a microorganism of the genus *Escherichia* for producing O-succinylhomoserine, in which activities of one or more of cystathionine gamma synthase and homoserine kinase are additionally attenuated or eliminated, compared to their endogenous activities. Specifically, the microorganism may be a microorganism for producing O-succinylhomoserine, in which activities of both of cystathionine gamma synthase and homoserine kinase are attenuated or eliminated, compared to their endogenous activities.

Cystathionine gamma synthase has an activity to convert O-succinylhomoserine into cystathionine. Cystathionine gamma synthase is encoded by metB gene. When the activity of this enzyme is attenuated or eliminated, O-succinylhomoserine may be accumulated without being converted into cystathionine.

Homoserine kinase catalyzes synthesis of O-phosphohomoserine from homoserine, and is encoded by thrB gene. When the activity of this enzyme is attenuated or eliminated, homoserine may not be converted into O-phosphohomoserine, and may be used in the production of O-succinylhomoserine.

In a specific embodiment of the present disclosure, the cystathionine gamma synthase may have an amino acid sequence of SEQ ID NO: 24, and the homoserine kinase may have an amino acid sequence of SEQ ID NO: 25. Further, the cystathionine gamma synthase and homoserine kinase may have amino acid sequences having 80% or higher, 90% or higher, or 95% % or higher homology with SEQ ID NOS: 24 and 25, respectively.

The term "attenuation" or "elimination" of the enzymatic activity, as used herein, means that expression of a gene encoding the corresponding enzyme or an activity of the enzyme is decreased, compared to the endogenous activity, or does not exist at all, and may be caused by modifying all or part of a base sequence of the gene encoding the corresponding enzyme or all or part of an expression regulatory sequence of the gene by deletion, substitution or insertion, or by a combination thereof.

The term "expression regulatory sequence", as used herein, is a base sequence regulating a gene expression, and refers to a segment capable of increasing or decreasing expression of a particular gene in a subject, and may include a promoter, a transcription factor binding site, etc., but is not limited thereto.

In a specific embodiment of the present disclosure, the microorganism may be a microorganism for producing O-succinylhomoserine, in which a homoserine O-succinyltransferase activity is additionally enhanced, compared to its endogenous activity.

Homoserine O-succinyltransferase is an enzyme that catalyzes production of O-succinylhomoserine from succinyl-CoA and homoserine, and is involved in a first step of a methionine biosynthetic pathway. A gene encoding this enzyme is commonly called metA, and its expression is suppressed by feedback regulation by methionine. Therefore, a mutant for expressing the gene at a high level by removing feedback regulation by methionine may be used.

In a specific embodiment of the present disclosure, the homoserine O-succinyltransferase may have an amino acid sequence of SEQ ID NO: 26. Further, the homoserine O-succinyltransferase may have an amino acid sequence having 80% or higher, 90% or higher, or 95% % or higher homology with SEQ ID NO: 26. Meanwhile, homoserine O-succinyltransferase, of which feedback regulation by methionine is removed, may have an amino acid sequence having 80% or higher, 90% or higher, or 95% % or higher homology with SEQ ID NO: 27 (metA11: Korean Patent Publication NO. 2009-0106365).

The term "enhancement" of the enzymatic activity, as used herein, means that activity of the corresponding enzyme is improved, compared to activity thereof before modification. Specifically, the enzymatic activity is increased by overexpression of a gene encoding the corresponding enzyme, compared to its endogenous activity, or activity of the enzyme encoded by the gene is increased by a mutation of the gene, compared to its endogenous activity, and the enhancement may be caused by increasing the copy number of the coding gene, substituting a promoter of the gene with a stronger promoter than the endogenous promoter, or modifying all or part of a base sequence of the gene on the chromosome or all or part of its expression regulatory sequence by deletion, substitution or insertion, or by a combination thereof.

In a specific embodiment of the present disclosure, the homoserine O-succinyltransferase may be encoded by a gene, in which a promoter of the gene encoding this enzyme is substituted with a stronger promoter than the endogenous promoter. For example, the promoter includes a known strong promoter, Ptac, Ptrc, Ppro, PR, PL, Prmf, PcysK, etc., but is not limited thereto.

In a specific embodiment of the present disclosure, the microorganism may be E. coli. The microorganism may be E. coli, in which the activity of glucose 6-phosphate-1-dehydrogenase is attenuated or eliminated, compared to the endogenous activity thereof, and activities of one or more of cystathionine gamma synthase and homoserine kinase are attenuated or eliminated, compared to their endogenous activities, respectively, and the activity of homoserine O-succinyltransferase is enhanced, compared to the endogenous activity thereof.

In a specific embodiment of the present disclosure, the microorganism may be E. coli, in which metA on the chromosome of E. coli is substituted with metA11 (SEQ ID NO: 27) which is a mutant prepared by removing feedback regulation by methionine, thrB and metB on the chromosome are deleted, and zwf is attenuated or eliminated.

In a specific embodiment of the present disclosure, the microorganism may be E. coli CC03-0156 which was deposited at the Korean Culture Center of Microorganisms (KCCM) on Nov. 22, 2013 with Accession NO: KCCM11487P.

Further, in a specific embodiment of the present disclosure, the microorganism may be a microorganism provided with a sucrose assimilation ability. The sucrose assimilation means an ability to metabolize sucrose as a carbon source or a metabolic source. The sucrose assimilation ability may be provided by introduction of a sucrose metabolic enzyme, for example, fructokinase, sucrose PTS permease, sucrose hydrolase, or invertase. For example, the sucrose assimilation ability may be provided by transformation with a recombinant vector (pAscrSM, SEQ ID NO: 28) including a gene encoding Scr-PTS enzyme derived from *Streptococcus mutans*, which is disclosed in Korean Patent Publication NO. 2010-0099572.

In a specific embodiment of the present disclosure, the microorganism may be E. coli, in which metA on the chromosome of E. coli is substituted with metA11 (SEQ ID NO: 27) which is a mutant prepared by removing feedback regulation by methionine, thrB and metB on the chromosome are deleted, and zwf is eliminated, and which is able to utilize a raw sugar by transformation with a recombinant vector including scrKYABR encoding fructokinase, sucrose PTS permease, sucrose hydrolase, and sucrose transcriptional regulator derived from sucrose assimilative *Streptococcus mutans*.

In an aspect of the present disclosure, provided is a method of producing O-succinylhomoserine, the method including steps of culturing microorganism of the genus *Escherichia* for producing O-succinylhomoserine, in which activity of glucose 6-phosphate-1-dehydrogenase is attenuated or eliminated compared to its endogenous activity, in a media, and recovering O-succinylhomoserine from the culture media or the cultured microorganism.

In the method of producing O-succinylhomoserine according to a specific embodiment of the present disclosure, culturing of the O-succinylhomoserine-producing strain may be performed in an appropriate medium and conditions known in the art. The culturing procedures may be readily adjusted by those skilled in the art according to the selected strain. Examples of the culturing procedures include batch type, continuous type and fed-batch type manners, but are not limited thereto. Various culturing procedures are disclosed in, for example, a literature ("Biochemical Engineering" by James M. Lee, Prentice-Hall International Editions, pp 138-176.).

A medium used for the culturing must meet the requirements for the culturing of a specific strain. The culture media for various microorganisms are described in a literature ("Manual of Methods for General Bacteriology" by the American Society for Bacteriology, Washington D.C., USA, 1981.). These media include a variety of carbon sources, nitrogen sources, and trace elements. The carbon source includes carbohydrates such as glucose, lactose, sucrose, fructose, maltose, starch and cellulose; fats such as soybean oil, sunflower oil, castor oil and coconut oil; fatty acids such as palmitic acid, stearic acid, and linoleic acid; alcohols such as glycerol and ethanol; and organic acids such as acetic acid. These carbon sources may be used alone or in combination. The nitrogen source includes organic nitrogen sources, such as peptone, yeast extract, gravy, malt extract, corn steep liquor (CSL) and bean flour, and inorganic nitrogen sources such as urea, ammonium sulfate, ammonium chloride, ammonium phosphate, ammonium carbonate and ammonium nitrate. These nitrogen sources may be used alone or in combination. Additionally, the medium may include potassium dihydrogen phosphate, dipotassium hydrogen phosphate, and corresponding sodium-containing salts thereof as a phosphorus source. Also, the medium may include a metal such as magnesium sulfate or iron sulfate. In addition, amino acids, vitamins and proper precursors may be added as well.

Further, to maintain the culture under aerobic conditions, oxygen or oxygen-containing gas (e.g., air) may be injected into the culture. A temperature of the culture is generally 20° C.-45° C., and specifically 25° C.-40° C. The culturing may be continued until production of L-methionine precursor reaches a desired level, and culturing time may be 10 hrs to 160 hrs.

Advantageous Effects of the Invention

An O-succinylhomoserine-producing strain of the present disclosure efficiently produces O-succinylhomoserine, which may be used in the production of L-methionine. L-methionine produced thereby may be widely used in the production of animal feeds or animal feed additives, as well as human foods or food additives.

MODE OF THE INVENTION

Hereinafter, the present disclosure will be described in more detail with reference to Examples. However, these Examples are for illustrative purposes only, and the scope of the present disclosure is not intended to be limited by these Examples.

REFERENCE EXAMPLE 1

Preparation of O-succinyl Homoserine-producing Strain 1-1. Deletion of metB Gene To increase accumulation of O-succinyl homoserine, a strain was prepared by deleting metB gene encoding cystathionine gamma synthase which is involved in the degradation of O-succinyl homoserine.

In a wild-type E. coli(K12) W3110 strain, metB gene encoding cystathionine gamma synthase was deleted. It is known that cystathionine gamma synthase binds with various methionine precursors in cells, thereby producing various by-products. Therefore, overexpression of cystathionine synthase may increase side reactions to reduce efficiency of intracellular reactions. For the deletion of metB gene, a FRT-one-step-PCR deletion method was performed (PNAS (2000), Vol. 197, p 6640-6645). First, PCR was performed using primers of SEQ ID NOS: 1 and 2 and a pKD3 vector (PNAS (2000) Vol. 197, pP 6640-6645) as a template to prepare a deletion cassette.

```
SEQ ID NO: 1:
5'-TTACTCTGGTGCCTGACATTTCACCGACAAAGCCCAGGGAACTTCAT

CACGTGTAGGCTGGAGCTGCTTC-3'

SEQ ID NO: 2:
5'-CGCTGCGCCAGCTCCATACGCGGCACCAGCGTTCGCAACCCACGTAG

CAGCATATGAATATCCTCCTTAG-3'
```

PCR conditions were 30 cycles of denaturation at 95° C. for 30 seconds, annealing at 55° C. for 30 seconds, and extension at 72° C. for 1 minute. A PCR product thus obtained was electrophoresed on a 1.0% agarose gel, followed by elution and purification of a band of 1.1 kb. A DNA fragment thus obtained was electroporated into E. coli(K12) W3110 strain previously transformed with a pKD46 vector (PNAS (2000) Vol. 97, p 6640-6645). For electroporation, W3110 strain transformed with pKD46 was cultured at 30° C. in LB medium containing 200 μg/L of ampicillin and 5 mM of L-arabinose until $OD_{600}$ reached 0.5. Then, the strain was washed three times with 10% glycerol. Electroporation was performed at 2500 V. The recovered strain was streaked on an LB plate medium containing 30 μg/L of chloramphenicol, followed by culturing at 37° C. for 1 day to 2 days. Then, a strain exhibiting resistance was selected.

PCR was performed by using the selected strain as a template and primers of SEQ ID NOS: 3 and 4 under the above-described conditions. The deletion of metB gene was confirmed by identifying a 1.5 kb-sized gene on a 1.0% agarose gel.

```
SEQ ID NO: 3:    5'-TATTCGCCGCTCCATTCAGC-3'

SEQ ID NO: 4:    5'-TACCCCTTGTTTGCAGCCCG-3'
```

The strain, in which deletion of metB gene was confirmed, was then transformed with a pCP20 vector (PNAS (2000) vol. 97, p 6640-6645) and cultured in LB medium containing 100 μg/L of ampicillin. Then, PCR was performed under the same conditions, and the elimination of chloramphenicol marker was confirmed by observing a smaller PCR product on a 1.0% agarose gel. Finally, a metB gene-deleted strain was prepared. The obtained methionine auxotrophic strain was named CC03-0132.

1-2. Deletion of thrB Gene

To increase production of O-succinylhomoserine from homoserine, thrB gene which is a gene encoding homoserine kinase was deleted. Particularly, when a threonine-producing strain is used, deletion of thrB gene is necessary because homoserine utilization activity is very strong. To delete thrB gene in the CC03-0132 strain prepared in Reference Example 1-1, the FRT-one-step-PCR deletion method was performed (PNAS (2000) Vol. 97, p 6640-6645). For the deletion of thrB gene, PCR was performed using primers of SEQ ID NOS: 5 and 6 and a pKD3 vector (PNAS (2000) Vol. 97, p 6640-6645) as a template to prepare a deletion cassette.

SEQ ID NO: 5:
5'-CATGGTTAAAGTTTATGCCCCGGCTTCCAGTGCCAATATGAGCGTCG

GGTGTGTAGGCTGGAGCTGCTTC-3'

SEQ ID NO: 6:
5'-GGAGATACCGCTCGCTACCGCGCCGATTTCCGCGACCGCCTGCCGCG

CCTCATATGAATATCCTCCTTAG-3'

PCR conditions were 30 cycles of denaturation at 95° C. for 30 seconds, annealing at 55° C. for 30 seconds, and extension at 72° C. for 1 minute. A PCR product thus obtained was electrophoresed on a 1.0% agarose gel, followed by elution and purification of a band of 1.1 kb. A DNA fragment thus obtained was electroporated into the CC03-0132 strain previously transformed with pKD46 vector (PNAS (2000) Vol. 97, p 6640-6645). For electroporation, CC03-0132 strain transformed with pKD46 was cultured at 30° C. in an LB medium containing 200 μg/L of ampicillin and 5 mM of L-arabinose until $OD_{600}$ reached 0.5. Then, the strain was washed three times with 10% glycerol. Electroporation was performed at 2500 V. The recovered strain was streaked on an LB plate medium containing 30 μg/L of chloramphenicol, followed by culturing at 37° C. for 1 day to 2 days. Then, a strain exhibiting resistance was selected.

PCR was performed by using the selected strain as a template and primers of SEQ ID NOS: 7 and 8 under the above-described conditions. The deletion of thrB gene was confirmed by identifying a 1.5 kb-sized gene on a 1.0% agarose gel.

SEQ ID NO: 7:     5'-ACTCGACGATCTCTTTGCC-3'

SEQ ID NO: 8:     5'-ACGCCGAGAGGATCTTCGCAG-3'

The strain thus confirmed was then transformed with a pCP20 vector (PNAS (2000) vol. 97, p 6640-6645) and cultured in an LB medium containing 100 μg/L of ampicillin. Then, PCR was performed under the same conditions, and the elimination of chloramphenicol marker was confirmed by observing a smaller PCR product on a 1.0% agarose gel. Finally, a thrB gene-deleted strain was prepared. The strain thus prepared was named CC03-0133.

1-3. Deletion of metA Gene

To introduce a feedback resistant metA gene into the chromosome, authentic chromosomal metA gene was deleted, based on the CC03-0133 strain which was prepared by deleting metB and thrB gene in E. coli(K12) W3110 strain. For the deletion of metA gene, the FRT-one-step-PCR deletion method was performed (PNAS (2000), Vol. 197, p 6640-6645). For the deletion of metA gene, PCR was performed using primers of SEQ ID NOS: 9 and 10 and a pKD3 vector (PNAS (2000) Vol. 197, pP 6640-6645) as a template to prepare a deletion cassette.

SEQ ID NO: 9:
5'-TCAGCTGTTGCGCATCGATTCCCGTGAATCGCGCAACACGCCCGCAG

AGCGTGTAGGCTGGAGCTGCTTC-3'

SEQ ID NO: 10:
5'-CCGTCACAAAGGCAATGCGCTTATCTTTACTGGCAAACAGATATGCA

TCCCATATGAATATCCTCCTTAG-3'

PCR conditions were 30 cycles of denaturation at 95° C. for 30 seconds, annealing at 55° C. for 30 seconds, and extension at 72° C. for 1 minute. A PCR product thus obtained was electrophoresed on a 1.0% agarose gel, followed by elution and purification of a band of 1.1 kb. A DNA fragment thus obtained was electroporated into CC03-0133 strain previously transformed with pKD46 vector (PNAS (2000) Vol. 97, p 6640-6645). For electroporation, CC03-0133 strain transformed with pKD46 was cultured at 30° C. in an LB medium containing 200 μg/L of ampicillin and 5 mM of L-arabinose until $OD_{600}$ reached 0.5. Then, the strain was washed three times with 10% glycerol. Electroporation was performed at 2500 V. The recovered strain was streaked on an LB plate medium containing 30 μg/L of chloramphenicol, followed by culturing at 37° C. for 1 day to 2 days. Then, a strain exhibiting resistance was selected.

PCR was performed by using the selected strain as a template and primers of SEQ ID NOS: 11 and 12 under the above-described conditions. The deletion of metA gene was confirmed by identifying a 1.5 kb-sized gene on a 1.0% agarose gel.

SEQ ID NO: 11:    5'-CTCATTAACGTTGGTTGTCA-3'

SEQ ID NO: 12"    5'-TATCTTGCTGCTGCTGAATG-3'

The strain thus confirmed was then transformed with a pCP20 vector (PNAS (2000) vol. 97, p 6640-6645) and cultured in an LB medium containing 100 μg/L of ampicillin. Then, PCR was performed under the same conditions, and the elimination of chloramphenicol marker was confirmed by observing a smaller PCR product on a 1.0% agarose gel. Finally, a metA gene-deleted strain was prepared. The strain thus prepared was named CC03-0134.

1.4. Insertion of metA11 Gene

Preparation of pSG Vector for metA11 Insertion

Most activity of homoserine succinyltransferase is regulated through feedback inhibition by a small amount of methionine added to a medium, and therefore, a mutant, in which feedback regulation by methionine was removed, was replaced for a large production of an L-methionine precursor, O-succinylhomoserine. To replace a wild-type chromosomal metA gene encoding homoserine succinyltransferase of E. coli by metA11 (SEQ ID NO: 27) encoding a mutant in which feedback regulation by methionine was removed, a pSG-metA11 vector for insertion was prepared. According to Korean Patent Publication NO. 2009-0106365, base sequence information of the metA11 gene was obtained, and on the basis of this base sequence, primers (SEQ ID NOS: 13 and 14) including from ATG to ORF of metA11 gene and recognition sites for restriction enzymes EcoRI and SacI were synthesized. PCR was performed using a pMetA11-CL plasmid as a template (Korean Patent Publication NO. 2009-0106365), which was prepared by ligating metA11 gene with a pCL1920 vector, and primers of the following SEQ ID NOS.

SEQ ID NO: 13:
5'-ggccgaattcatgccgattcgtgtgccgga-3'

SEQ ID NO: 14:
5'-ggccgagctcgttaatccagcgttggattca-3'

PCR was performed using pfu-X DNA polymerase (SolGent; SPX16-R250), and PCR conditions were 30 cycles of denaturation at 95° C. for 30 seconds, annealing at 55° C. for 30 seconds, and extension at 72° C. for 2 minutes. As a result, a PCR product of amplified metA11 ORF including recognition sites for restriction enzymes EcoRI and SacI at both ends was obtained. The metA11 gene obtained by PCR was treated with restriction enzymes EcoRI and SacI, and ligated with a pSG76-C vector (Nucleic Acids Res. 1999 Nov. 15; 27(22):4409-15) which was treated with restriction enzymes EcoRI and SacI to clone the gene. Finally, a metA11 gene-cloned pSG-metA11 recombinant vector was prepared.

Preparation of metA11 Gene-inserted Strain

The CC03-0134 strain obtained in Reference Example 1-3 was transformed with the prepared pSG-metA11 which was a vector for metA11 gene insertion, and cultured in an LB Cm (10 g/L of yeast extract, 5 g/L of NaCl, 10 g/L of tryptone, and 30 μg/L of chloramphenicol) medium. Then, a colony having chloramphenicol resistance was selected. The selected transformant was a strain, in which the pSG-metA11 vector was primarily inserted into the chromosomal metA. The metA11 gene-inserted strain was transformed with a pST76-ASceP vector (Nucleic Acids Res. 1999 Nov. 15; 27(22):4409-15) expressing I-SceI which is a restriction enzyme digesting I-SceI in the pSG vector, and a strain growing in LB-Amp (10 g/L of yeast extract, 5 g/L of NaCl, 10 g/L of tryptone, and 100 μg/L of chloramphenicol) was selected. This strain thus selected was a strain in which wild-type metA was replaced by metA11 and inserted pSG76-C vector was removed. This strain was named E. coli CC03-0038.

EXAMPLE 1

Attenuation and Deletion of Zwf Gene 1-1. Attenuation of Zwf Gene

Preparation of pSG Vector for Replacement of Start Codon of Zwf Gene

To attenuate zwf gene in the CC03-0038 strain prepared in Reference Example 1-4, a method of replacing a start codon ATG of the ORF region of zwf gene by GTG was applied. PCR was performed using primers of SEQ ID NOS: 15 and 16, and SEQ ID NOS: 17 and 18 and the genome of E. coli W3110 as a template.

```
SEQ ID NO: 15:
5'-ggccgaattcctgaaagaaatcgaaatgcag-3'

SEQ ID NO: 16:
5'-cacgtcattctccttaagaattc-3'

SEQ ID NO: 17:
5'-gaattcttaaggagaatgacgtg-3'

SEQ ID NO: 18:
5'-ggccgagctcgggcatggcaaagtagttaatg-3'
```

PCR was performed using pfu-X DNA polymerase (Sol-Gent; SPX16-R250), and PCR conditions were 30 cycles of denaturation at 95° C. for 30 seconds; annealing at 55° C. for 30 seconds; and extension at 72° C. for 1 minute. SOEing (Splicing by Overlap Extension) PCR was performed using the two fragments thus obtained as templates. As a result, a zwf region including recognition sites for restriction enzymes EcoRI and SacI at both ends and the start codon GTG was obtained. Restriction enzymes EcoRI and SacI were treated to the ends of the obtained fragment including the recognition sites for the enzymes, and cloned into a pSG76-C vector (Nucleic Acids Res. 1999 Nov. 15; 27(22): 4409-15) treated with restriction enzymes EcoRI and SacI by ligation. Finally, a pSG-zwf(GTG) recombinant vector was prepared.

Preparation of Strain Having Replacement of Start Codon of Zwf Gene pSG-zwf(GTG), which was prepared for replacement of the start codon of zwf gene as described above, was transformed into the CC03-0038 strain prepared in Reference Example 1-4, and cultured in an LB_Cm (10 g/L of yeast extract, 5 g/L of NaCl, 10 g/L of tryptone, and 30 μg/L of chloramphenicol) medium. Then, a colony having chloramphenicol resistance was selected. The selected transformant was a strain, in which the pSG-zwf(GTG) vector was primarily inserted into the chromosomal zwf. The selected strain was transformed with a pST76-ASceP (Nucleic Acids Res. 1999 Nov. 15; 27(22):4409-15) expressing I-SceI which is a restriction enzyme digesting I-SceI in the pSG vector, and a strain growing in LB-Amp (10 g/L of yeast extract, 5 g/L of NaCl, 10 g/L of tryptone, and 100 μg/L of chloramphenicol) was selected. This strain thus selected was a strain in which zwf gene was attenuated by replacing the start codon ATG of zwf gene by GTG and then inserted pSG76-C vector was removed. This strain was named CC03-0038zwfGTG.

1-2. Deletion of Zwf Gene

To delete zwf gene in the CC03-0038 strain prepared in Reference Example 1-4, the FRT-one-step-PCR deletion method was performed (PNAS (2000) Vol. 97, p 6640-6645). For deletion of the zwf gene, PCR was performed using primers of SEQ ID NOS: 19 and 20 and the pKD3 vector (PNAS (2000) vol. 97 P6640-6645) as a template to prepare a deletion cassette.

```
SEQ ID NO: 19:
5'-CAAGTATACCCTGGCTTAAGTACCGGGTTAGTTAACTTAAGGAGAAT
GACGTGTAGGCTGGAGCTGCTTC-3'

SEQ ID NO: 20:
5'-CTGCGCAAGATCATGTTACCGGTAAAATAACCATAAAGGATAAGCGC
AGATACATATGAATATCCTCCTTAG-3'
```

PCR conditions were 30 cycles of denaturation at 95° C. for 30 seconds, annealing at 55° C. for 30 seconds, and extension at 72° C. for 1 minute. A PCR product thus obtained was electrophoresed on a 1.0% agarose gel, followed by elution and purification of a band of 1.1 kb. A DNA fragment thus obtained was electroporated into CC03-0038 strain previously transformed with pKD46 vector (PNAS (2000), Vol. 97, p 6640-6645). For electroporation, CC03-0038 strain transformed with pKD46 was cultured at 30° C. in an LB medium containing 200 μg/L of ampicillin and 5 mM of arabinose until $OD_{600}$ reached 0.5. Then, the strain was washed three times with 10% glycerol. Electroporation was performed at 2500 V. The recovered strain was streaked on an LB plate medium containing 30 μg/L of chloramphenicol, followed by culturing at 37° C. for 1 day to 2 days. Then, a strain exhibiting resistance was selected.

PCR was performed by using the selected strain as a template and primers of SEQ ID NOS: 21 and 22 under the above-described conditions. The deletion of zwf gene was confirmed by identifying a 2 kb-sized gene on a 1.0% agarose gel.

```
SEQ ID NO: 21:     5'-CATAACATGATCAGTGTCAGAT-3'

SEQ ID NO: 22:     5'-CGCGTAACAATTGTGGATTCAT-3'
```

The strain thus identified was named CC03-0156.

1-3. Preparation of O-succinyl Homoserine-Producing Strain Based on Threonine-producing Strain A threonine-producing strain, *E. coli* KCCM 10541P disclosed in International Patent WO 2005/075625 was used to delete metB, thrB and metA genes in the same manner as described in Reference Example 1, and then feedback-resistant metA11 gene was introduced to prepare a strain for producing O-succinylhomoserine, which was named CJM2-A11. Additionally, a zwf gene-deleted strain was prepared in the same manner as described in Example 1-2, and named CJM2-A11Z.

EXAMPLE 2

Fermentation for O-succinylhomoserine Production

To examine the effect of zwf gene deletion in the strain prepared in Example 1, Erlenmeyer flask culture was performed. A flask medium composition is the same as in the following Table 1.

Further, a pAscrSM plasmid (SEQ ID NO: 28) having a scrKYABR (hereinbelow, referred to as "scrO") sequence described in Korean Patent Publication NO. 2009-0018128 was introduced to prepare a strain capable of utilizing a raw sugar, followed by flask culturing. A flask medium composition is the same as in the following Table 2. The strains prepared by the above method were named CC03-0038/pAscrSM, CC03-0038zwfGTG/pAscrSM, CC03-0156/pAscrSM, CJM2-A11/pAscrSM and CJM2-A11Z/pAscrSM, respectively.

TABLE 1

Flask medium composition

| Composition | Stock | Concentration (per liter) | Vol (ml) |
|---|---|---|---|
| Glucose | | 40 g | 200 |
| $KH_2PO_4$ | | 2 g | 100 |
| Ammonium sulfate | | 17 g | 500 |
| $MgSO_4 \cdot 7H_2O$ | | 1 g | |
| Yeast extract | | 2 g | |
| Methionine | | 0.4 g | |
| Threonine | | 1 g | |
| $MnSO_4 \cdot 7H_2O$ | 10 mg/ml | 0.01 g (stock 1 ml) | |
| $ZnSO_4 \cdot 7H_2O$ | 1 mg/ml | 0.01 g (stock 10 ml) | |
| $FeSO_4 \cdot 7H_2O$ | 10 mg/ml | 10 mg (stock 1 ml) | |
| Calcium carbonate | | 30 g | 200 |

TABLE 2

Flask medium composition

| Composition | Stock | Concentration (per liter) | Vol (ml) |
|---|---|---|---|
| Raw sugar | | 60 g | 200 |
| $KH_2PO_4$ | | 2 g | 100 |
| Ammonium sulfate | | 25 g | 500 |
| $MgSO_4 \cdot 7H_2O$ | | 1 g | |
| Yeast extract | | 2 g | |
| Methionine | | 0.4 g | |
| Threonine | | 1 g | |
| $MnSO_4 \cdot 7H_2O$ | 10 mg/ml | 0.01 g (stock 1 ml) | |
| $ZnSO_4 \cdot 7H_2O$ | 1 mg/ml | 0.01 g (stock 10 ml) | |
| $FeSO_4 \cdot 7H_2O$ | 10 mg/ml | 10 mg (stock 1 ml) | |
| Calcium carbonate | | 30 g | 200 |

Each of CC03-0038, CC03-0038zwfGTG, CC03-0156, CJM2-A11, CJM2-A11Z, CC03-0038/pAscrSM, CC03-0038zwfGTG/pAscrSM, CC03-0156/pAscrSM, CJM2-A11/pAscrSM and CJM2-A11Z/pAscrSM was inoculated on LB plate media and cultured at 33° C. for overnight. A single colony was inoculated in 2 ml of LB medium, followed by culturing at 33° C. for 2 hours. The culture was inoculated in a 250 ml-Erlenmeyer flask containing 25 ml of the flask medium at $OD_{600}$=0.5, followed by culturing at 33° C., 200 rpm for 48 hours. HPLC was performed to compare O-succinylhomoserine productions. The results are given in the following Table 3.

TABLE 3

Production of O-succinyl homoserine by flask culturing

| Strain | OD | Sugar consumption (g/L) | Production amount of O-succinyl homoserine (g/L) | Production amount of homoserine (g/L) |
|---|---|---|---|---|
| CC03-0038 | 6 | 40 | 4.5 | 0.4 |
| CC03-0038zwfGTG | 6 | 40 | 4.9 | 0.4 |
| CC03-0156 (CC03-0038Δzwf) | 5 | 40 | 6.0 | 0.3 |
| CJM2-A11 | 18.2 | 40 | 10.5 | 1.1 |
| CJM2-A11Z (CJM2-A11Δzwf) | 16.4 | 40 | 13.0 | 0.7 |
| CC03-0038/pAscrSM | 12.2 | 60 | 7.0 | 0.7 |
| CC03-0038zwfGTG/pAscrSM | 11.9 | 60 | 8.1 | 0.7 |
| CC03-0156/pAscrSM | 11.8 | 60 | 9.8 | 0.5 |
| CJM2-A11/pAscrSM | 18.5 | 60 | 15.0 | 1.5 |
| CJM2-A11Z/pAscrSM | 17.2 | 60 | 19.3 | 1.0 |

The results of flask culturing showed that zwf gene-attenuated or deleted CC03-0038zwfGTG, CC03-0156, CJM2-A11Z, CC03-0038zwfGTG/pAscrSM, CC03-0156/pAscrSM, and CJM2-A11Z/pAscrSM strains showed 8.9% to 40.0% higher O-succinylhomoserine productions than respective control strains. Further, a reduction in the homoserine production was observed, suggesting that production of succinyl-CoA was increased by enhancement of the TCA cycle.

The present inventors confirmed that O-succinylhomoserine may be produced in a high yield by attenuation or deletion of zwf gene in CC03-0038 strain and CJM2-A11 strain. The CC03-0156 strain was deposited under the Budapest Treaty at the Korean Culture Center of Microorganisms (KCCM) on Nov. 22, 2013 with Accession NO: KCCM11487P.

In terms of application of zwf gene to enhancement of the TCA cycle, it is to be understood that attenuation or deletion of zwf gene is not limited to *E. coli*, but equally applied to all microorganisms having the TCA cycle, including genus *Escherichia*, genus *Corynebacterium*, yeast, etc., for the high-yield production of O-succinylhomoserine.

The invention claimed is:

1. A method of producing O-succinylhomoserine, the method comprising:
culturing a genetically modified microorganism in a culture media, and
recovering the O-succinylhomoserine from the culture media and/or recovering the O-succinylhomoserine from the cultured genetically modified microorganism,
wherein the genetically modified microorganism comprises:
(a) a genetic modification of an endogenous gene encoding a glucose 6-phosphate-1-dehydrogenase to decrease or eliminate expression of the endogenous gene encoding the glucose 6-phosphate-1-dehydrogenase, compared to the expression of the endogenous gene encoding the glucose 6-phosphate-1-dehydrogenase in the microorganism prior to the genetic modification,
(b) a genetic modification of an endogenous gene encoding a cystathionine gamma synthase to decrease or eliminate expression of the endogenous gene encoding the cystathionine gamma synthase, compared to the expression of the endogenous gene encoding the cystathionine gamma synthase in the microorganism prior to the genetic modification,
(c) a genetic modification of an endogenous gene encoding a homoserine kinase to decrease or eliminate expression of the endogenous gene encoding the homoserine kinase, compared to the expression of the endogenous gene encoding the homoserine kinase in the microorganism prior to the genetic modification, and
(d) a genetic modification to increase a homoserine O-succinyltransferase activity (i) by expressing a gene encoding the homoserine O-succinyltransferase, (ii) by mutation of the gene encoding the homoserine O-succinyltransferase to remove feedback regulation by methionine, (iii) by increasing the copy number of the gene encoding the homoserine O-succinyltransferase, or (iv) by substituting the endogenous promoter of the gene encoding the homoserine O-succinyltransferase with a promoter that is stronger than the endogenous promoter;
wherein after culturing the genetically modified microorganism an amount of the O-succinylhomoserine produced by the cultured genetically modified microorganism is 8.9% to 40% greater than an amount of the O-succinylhomoserine produced by the corresponding cultured microorganism having an intact endogenous gene encoding the glucose 6-phosphate-1-dehydrogenase, and wherein the genetically modified microorganism is *Escherichia coli*.

2. The method according to claim 1, wherein the glucose 6-phosphate-1-dehydrogenase has the amino acid sequence of SEQ ID NO: 23.

3. The method according to claim 1, wherein the cystathionine gamma synthase has the amino acid sequence of SEQ ID NO: 24, and the homoserine kinase has the amino acid sequence of SEQ ID NO: 25.

4. The method according to claim 1, wherein the homoserine O-succinyltransferase has the amino acid sequence of SEQ ID NO: 26.

5. The method according to claim 1, wherein the genetically modified microorganism further comprises a recombinant vector comprising genes encoding a fructokinase, a sucrose PTS permease, a sucrose hydrolase, and a sucrose transcriptional regulator derived from *Streptococcus mutans*.

\* \* \* \* \*

SEQUENCE LISTING

<160> NUMBER OF SEQ ID NOS: 28

<210> SEQ ID NO 1
<211> LENGTH: 70
<212> TYPE: DNA
<213> ORGANISM: Artificial Sequence
<220> FEATURE:
<223> OTHER INFORMATION: Forward primer of metB deletion cassette

<400> SEQUENCE: 1
ttactctggt gcctgacatt tcaccgacaa agcccaggga acttcatcac gtgtaggctg     60
gagctgcttc                                                            70

<210> SEQ ID NO 2
<211> LENGTH: 70
<212> TYPE: DNA
<213> ORGANISM: Artificial Sequence
<220> FEATURE:
<223> OTHER INFORMATION: Reverse primer of metB deletion cassette

<400> SEQUENCE: 2
cgctgcgcca gctccatacg cggcaccagc gttcgcaacc cacgtagcag catatgaata     60
tcctccttag                                                            70

<210> SEQ ID NO 3
<211> LENGTH: 20
<212> TYPE: DNA
<213> ORGANISM: Artificial Sequence
<220> FEATURE:
<223> OTHER INFORMATION: Forward primer for deleted metB

<400> SEQUENCE: 3
tattcgccgc tccattcagc                                                 20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for deleted metB

<400> SEQUENCE: 4
taccccttgt ttgcagcccg                                                 20

<210> SEQ ID NO 5
<211> LENGTH: 70
<212> TYPE: DNA
<213> ORGANISM: Artificial Sequence
<220> FEATURE:
<223> OTHER INFORMATION: Forward primer for thrB deletion cassette

<400> SEQUENCE: 5
catggttaaa gtttatgccc cggcttccag tgccaatatg agcgtcgggt gtgtaggctg     60
gagctgcttc                                                            70

<210> SEQ ID NO 6
<211> LENGTH: 70
<212> TYPE: DNA
<213> ORGANISM: Artificial Sequence
<220> FEATURE:
<223> OTHER INFORMATION: Reverse primer for thrB deletion cassette

<400> SEQUENCE: 6
ggagataccg ctcgctaccg cgccgatttc cgcgaccgcc tgccgcgcct catatgaata     60

```
tcctccttag                                                             70

<210> SEQ ID NO 7
<211> LENGTH: 19
<212> TYPE: DNA
<213> ORGANISM: Artificial Sequence
<220> FEATURE:
<223> OTHER INFORMATION: Forward primer for deleted thrB

<400> SEQUENCE: 7
actcgacgat ctctttgcc                                                   19

<210> SEQ ID NO 8
<211> LENGTH: 21
<212> TYPE: DNA
<213> ORGANISM: Artificial Sequence
<220> FEATURE:
<223> OTHER INFORMATION: Reverse primer for deleted thrB

<400> SEQUENCE: 8
acgccgagag gatcttcgca g                                                21

<210> SEQ ID NO 9
<211> LENGTH: 70
<212> TYPE: DNA
<213> ORGANISM: Artificial Sequence
<220> FEATURE:
<223> OTHER INFORMATION: Forward primer for metA deletion cassette

<400> SEQUENCE: 9
tcagctgttg cgcatcgatt cccgtgaatc gcgcaacacg cccgcagagc gtgtaggctg      60
gagctgcttc                                                             70

<210> SEQ ID NO 10
<211> LENGTH: 70
<212> TYPE: DNA
<213> ORGANISM: Artificial Sequence
<220> FEATURE:
<223> OTHER INFORMATION: Reverse primer for metA deletion cassette

<400> SEQUENCE: 10
ccgtcacaaa ggcaatgcgc ttatctttac tggcaaacag atatgcatcc catatgaata      60
tcctccttag                                                             70

<210> SEQ ID NO 11
<211> LENGTH: 20
<212> TYPE: DNA
<213> ORGANISM: Artificial Sequence
<220> FEATURE:
<223> OTHER INFORMATION: Forwad primer for deleted metA

<400> SEQUENCE: 11
ctcattaacg ttggttgtca                                                  20

<210> SEQ ID NO 12
<211> LENGTH: 20
<212> TYPE: DNA
<213> ORGANISM: Artificial Sequence
<220> FEATURE:
<223> OTHER INFORMATION: Reverse primer for deleted metA

<400> SEQUENCE: 12
tatcttgctg ctgctgaatg                                                  20
```

```
<210> SEQ ID NO 13
<211> LENGTH: 30
<212> TYPE: DNA
<213> ORGANISM: Artificial Sequence
<220> FEATURE:
<223> OTHER INFORMATION: Forward primer for metA11

<400> SEQUENCE: 13
ggccgaattc atgccgattc gtgtgccgga                                    30

<210> SEQ ID NO 14
<211> LENGTH: 31
<212> TYPE: DNA
<213> ORGANISM: Artificial Sequence
<220> FEATURE:
<223> OTHER INFORMATION: Reverse primer for metA11

<400> SEQUENCE: 14
ggccgagctc gttaatccag cgttggattc a                                  31

<210> SEQ ID NO 15
<211> LENGTH: 31
<212> TYPE: DNA
<213> ORGANISM: Artificial Sequence
<220> FEATURE:
<223> OTHER INFORMATION: Forwad primer for start codon substitution of
      zwf

<400> SEQUENCE: 15
ggccgaattc ctgaaagaaa tcgaaatgca g                                  31

<210> SEQ ID NO 16
<211> LENGTH: 23
<212> TYPE: DNA
<213> ORGANISM: Artificial Sequence
<220> FEATURE:
<223> OTHER INFORMATION: Reverse primer for start codon substitution of
      zwf

<400> SEQUENCE: 16
cacgtcattc tccttaagaa ttc                                           23

<210> SEQ ID NO 17
<211> LENGTH: 23
<212> TYPE: DNA
<213> ORGANISM: Artificial Sequence
<220> FEATURE:
<223> OTHER INFORMATION: Forward primer 2 for start codon substitution
      of zwf

<400> SEQUENCE: 17
gaattcttaa ggagaatgac gtg                                           23

<210> SEQ ID NO 18
<211> LENGTH: 32
<212> TYPE: DNA
<213> ORGANISM: Artificial Sequence
<220> FEATURE:
<223> OTHER INFORMATION: Reverse primer 2 for start codon substitution
      of zwf

<400> SEQUENCE: 18
ggccgagctc gggcatggca aagtagttaa tg                                 32

<210> SEQ ID NO 19
<211> LENGTH: 70
```

<212> TYPE: DNA
<213> ORGANISM: Artificial Sequence
<220> FEATURE:
<223> OTHER INFORMATION: Forward primer for zwf deletion cassette

<400> SEQUENCE: 19
caagtatacc ctggcttaag taccgggtta gttaacttaa ggagaatgac gtgtaggctg    60
gagctgcttc    70

<210> SEQ ID NO 20
<211> LENGTH: 72
<212> TYPE: DNA
<213> ORGANISM: Artificial Sequence
<220> FEATURE:
<223> OTHER INFORMATION: Reverse primer for zwf deletion cassette

<400> SEQUENCE: 20
ctgcgcaaga tcatgttacc ggtaaaataa ccataaagga taagcgcaga tacatatgaa    60
tatcctcctt ag    72

<210> SEQ ID NO 21
<211> LENGTH: 22
<212> TYPE: DNA
<213> ORGANISM: Forward primer for deleted zwf

<400> SEQUENCE: 21
cataacatga tcagtgtcag at    22

<210> SEQ ID NO 22
<211> LENGTH: 22
<212> TYPE: DNA
<213> ORGANISM: Artificial Sequence
<220> FEATURE:
<223> OTHER INFORMATION: Reverse primer for deleted zwf

<400> SEQUENCE: 22
cgcgtaacaa ttgtggattc at    22

<210> SEQ ID NO 23
<211> LENGTH: 491
<212> TYPE: PRT
<213> ORGANISM: Escherichia coli

<400> SEQUENCE: 23

Met Ala Val Thr Gln Thr Ala Gln Ala Cys Asp Leu Val Ile Phe Gly
1               5                   10                  15

Ala Lys Gly Asp Leu Ala Arg Arg Lys Leu Leu Pro Ser Leu Tyr Gln
            20                  25                  30

Leu Glu Lys Ala Gly Gln Leu Asn Pro Asp Thr Arg Ile Ile Gly Val
        35                  40                  45

Gly Arg Ala Asp Trp Asp Lys Ala Ala Tyr Thr Lys Val Val Arg Glu
    50                  55                  60

Ala Leu Glu Thr Phe Met Lys Glu Thr Ile Asp Glu Gly Leu Trp Asp
65                  70                  75                  80

Thr Leu Ser Ala Arg Leu Asp Phe Cys Asn Leu Asp Val Asn Asp Thr
                85                  90                  95

Ala Ala Phe Ser Arg Leu Gly Ala Met Leu Asp Gln Lys Asn Arg Ile
            100                 105                 110

Thr Ile Asn Tyr Phe Ala Met Pro Pro Ser Thr Phe Gly Ala Ile Cys
        115                 120                 125

```
Lys Gly Leu Gly Glu Ala Lys Leu Asn Ala Lys Pro Ala Arg Val Val
    130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
                165                 170                 175

His Tyr Leu Gly Lys Glu Thr Val Leu Asn Leu Leu Ala Leu Arg Phe
                180                 185                 190

Ala Asn Ser Leu Phe Val Asn Asn Trp Asp Asn Arg Thr Ile Asp His
            195                 200                 205

Val Glu Ile Thr Val Ala Glu Glu Val Gly Ile Glu Gly Arg Trp Gly
    210                 215                 220

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
                245                 250                 255

Ala Asp Ser Ile Arg Asp Glu Lys Val Lys Val Leu Lys Ser Leu Arg
                260                 265                 270

Arg Ile Asp Arg Ser Asn Val Arg Glu Lys Thr Val Arg Gly Gln Tyr
            275                 280                 285

Thr Ala Gly Phe Ala Gln Gly Lys Lys Val Pro Gly Tyr Leu Glu Glu
    290                 295                 300

Glu Gly Ala Asn Lys Ser Ser Asn Thr Glu Thr Phe Val Ala Ile Arg
305                 310                 315                 320

Val Asp Ile Asp Asn Trp Arg Trp Ala Gly Val Pro Phe Tyr Leu Arg
                325                 330                 335

Thr Gly Lys Arg Leu Pro Thr Lys Cys Ser Glu Val Val Val Tyr Phe
                340                 345                 350

Lys Thr Pro Glu Leu Asn Leu Phe Lys Glu Ser Trp Gln Asp Leu Pro
            355                 360                 365

Gln Asn Lys Leu Thr Ile Arg Leu Gln Pro Asp Glu Gly Val Asp Ile
    370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                405                 410                 415

Leu Ala Asp Ala Tyr Glu Arg Leu Leu Leu Glu Thr Met Arg Gly Ile
                420                 425                 430

Gln Ala Leu Phe Val Arg Arg Asp Glu Val Glu Glu Ala Trp Lys Trp
            435                 440                 445

Val Asp Ser Ile Thr Glu Ala Trp Ala Met Asp Asn Asp Ala Pro Lys
    450                 455                 460

Pro Tyr Gln Ala Gly Thr Trp Gly Pro Val Ala Ser Val Ala Met Ile
465                 470                 475                 480

Thr Arg Asp Gly Arg Ser Trp Asn Glu Phe Glu
                485                 490

<210> SEQ ID NO 24
<211> LENGTH: 386
<212> TYPE: PRT
<213> ORGANISM: Escherichia coli

<400> SEQUENCE: 24

Met Thr Arg Lys Gln Ala Thr Ile Ala Val Arg Ser Gly Leu Asn Asp
1               5                   10                  15
```

Asp Glu Gln Tyr Gly Cys Val Pro Pro Ile His Leu Ser Ser Thr
            20                  25                  30

Tyr Asn Phe Thr Gly Phe Asn Glu Pro Arg Ala His Asp Tyr Ser Arg
        35                  40                  45

Arg Gly Asn Pro Thr Arg Asp Val Val Gln Arg Ala Leu Ala Glu Leu
50                  55                  60

Glu Gly Gly Ala Gly Ala Val Leu Thr Asn Thr Gly Met Ser Ala Ile
65                  70                  75                  80

His Leu Val Thr Thr Val Phe Leu Lys Pro Gly Asp Leu Leu Val Ala
                85                  90                  95

Pro His Asp Cys Tyr Gly Gly Ser Tyr Arg Leu Phe Asp Ser Leu Ala
            100                 105                 110

Lys Arg Gly Cys Tyr Arg Val Leu Phe Val Asp Gln Gly Asp Glu Gln
        115                 120                 125

Ala Leu Arg Ala Ala Leu Ala Glu Lys Pro Lys Leu Val Leu Val Glu
    130                 135                 140

Ser Pro Ser Asn Pro Leu Leu Arg Val Val Asp Ile Ala Lys Ile Cys
145                 150                 155                 160

His Leu Ala Arg Glu Val Gly Ala Val Ser Val Val Asp Asn Thr Phe
                165                 170                 175

Leu Ser Pro Ala Leu Gln Asn Pro Leu Ala Leu Gly Ala Asp Leu Val
            180                 185                 190

Leu His Ser Cys Thr Lys Tyr Leu Asn Gly His Ser Asp Val Val Ala
        195                 200                 205

Gly Val Val Ile Ala Lys Asp Pro Asp Val Val Thr Glu Leu Ala Trp
    210                 215                 220

Trp Ala Asn Asn Ile Gly Val Thr Gly Gly Ala Phe Asp Ser Tyr Leu
225                 230                 235                 240

Leu Leu Arg Gly Leu Arg Thr Leu Val Pro Arg Met Glu Leu Ala Gln
                245                 250                 255

Arg Asn Ala Gln Ala Ile Val Lys Tyr Leu Gln Thr Gln Pro Leu Val
            260                 265                 270

Lys Lys Leu Tyr His Pro Ser Leu Pro Glu Asn Gln Gly His Glu Ile
        275                 280                 285

Ala Ala Arg Gln Gln Lys Gly Phe Gly Ala Met Leu Ser Phe Glu Leu
    290                 295                 300

Asp Gly Asp Glu Gln Thr Leu Arg Arg Phe Leu Gly Gly Leu Ser Leu
305                 310                 315                 320

Phe Thr Leu Ala Glu Ser Leu Gly Gly Val Glu Ser Leu Ile Ser His
                325                 330                 335

Ala Ala Thr Met Thr His Ala Gly Met Ala Pro Glu Ala Arg Ala Ala
            340                 345                 350

Ala Gly Ile Ser Glu Thr Leu Leu Arg Ile Ser Thr Gly Ile Glu Asp
        355                 360                 365

Gly Glu Asp Leu Ile Ala Asp Leu Glu Asn Gly Phe Arg Ala Ala Asn
    370                 375                 380

Lys Gly
385

<210> SEQ ID NO 25
<211> LENGTH: 310
<212> TYPE: PRT
<213> ORGANISM: Escherichia coli

<400> SEQUENCE: 25

```
Met Val Lys Val Tyr Ala Pro Ala Ser Ser Ala Asn Met Ser Val Gly
1               5                   10                  15

Phe Asp Val Leu Gly Ala Ala Val Thr Pro Val Asp Gly Ala Leu Leu
            20                  25                  30

Gly Asp Val Thr Val Glu Ala Ala Glu Thr Phe Ser Leu Asn Asn
        35                  40                  45

Leu Gly Arg Phe Ala Asp Lys Leu Pro Ser Glu Pro Arg Glu Asn Ile
    50                  55                  60

Val Tyr Gln Cys Trp Glu Arg Phe Cys Gln Glu Leu Gly Lys Gln Ile
65                  70                  75                  80

Pro Val Ala Met Thr Leu Glu Lys Asn Met Pro Ile Gly Ser Gly Leu
                85                  90                  95

Gly Ser Ser Ala Cys Ser Val Val Ala Ala Leu Met Ala Met Asn Glu
            100                 105                 110

His Cys Gly Lys Pro Leu Asn Asp Thr Arg Leu Leu Ala Leu Met Gly
        115                 120                 125

Glu Leu Glu Gly Arg Ile Ser Gly Ser Ile His Tyr Asp Asn Val Ala
    130                 135                 140

Pro Cys Phe Leu Gly Gly Met Gln Leu Met Ile Glu Glu Asn Asp Ile
145                 150                 155                 160

Ile Ser Gln Gln Val Pro Gly Phe Asp Glu Trp Leu Trp Val Leu Ala
                165                 170                 175

Tyr Pro Gly Ile Lys Val Ser Thr Ala Glu Ala Arg Ala Ile Leu Pro
            180                 185                 190

Ala Gln Tyr Arg Arg Gln Asp Cys Ile Ala His Gly Arg His Leu Ala
        195                 200                 205

Gly Phe Ile His Ala Cys Tyr Ser Arg Gln Pro Glu Leu Ala Ala Lys
    210                 215                 220

Leu Met Lys Asp Val Ile Ala Glu Pro Tyr Arg Glu Arg Leu Leu Pro
225                 230                 235                 240

Gly Phe Arg Gln Ala Arg Gln Ala Val Ala Glu Ile Gly Ala Val Ala
                245                 250                 255

Ser Gly Ile Ser Gly Ser Gly Pro Thr Leu Phe Ala Leu Cys Asp Lys
            260                 265                 270

Pro Glu Thr Ala Gln Arg Val Ala Asp Trp Leu Gly Lys Asn Tyr Leu
        275                 280                 285

Gln Asn Gln Glu Gly Phe Val His Ile Cys Arg Leu Asp Thr Ala Gly
    290                 295                 300

Ala Arg Val Leu Glu Asn
305             310
```

<210> SEQ ID NO 26
<211> LENGTH: 309
<212> TYPE: PRT
<213> ORGANISM: Escherichia coli

<400> SEQUENCE: 26

```
Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Pro Gly Gln Glu
            20                  25                  30

Ile Arg Pro Leu Lys Val Leu Ile Leu Asn Leu Met Pro Lys Lys Ile
        35                  40                  45
```

```
Glu Thr Glu Asn Gln Phe Leu Arg Leu Leu Ser Asn Ser Pro Leu Gln
 50                  55                  60

Val Asp Ile Gln Leu Leu Arg Ile Asp Ser Arg Glu Ser Arg Asn Thr
 65                  70                  75                  80

Pro Ala Glu His Leu Asn Asn Phe Tyr Cys Asn Phe Glu Asp Ile Gln
                 85                  90                  95

Asp Gln Asn Phe Asp Gly Leu Ile Val Thr Gly Ala Pro Leu Gly Leu
            100                 105                 110

Val Gly Phe Asn Asp Val Ala Tyr Trp Pro Gln Ile Lys Gln Val Leu
            115                 120                 125

Glu Trp Ser Lys Asp His Val Thr Ser Thr Leu Ser Val Cys Trp Ala
130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
            195                 200                 205

Glu Ile Leu Ala Glu Thr Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
            275                 280                 285

Leu Asn Tyr Tyr Val Tyr Gln Ile Thr Pro Tyr Asp Leu Arg His Met
            290                 295                 300

Asn Pro Thr Leu Asp
305

<210> SEQ ID NO 27
<211> LENGTH: 930
<212> TYPE: DNA
<213> ORGANISM: Artificial Sequence
<220> FEATURE:
<223> OTHER INFORMATION: metA11

<400> SEQUENCE: 27
atgccgattc gtgtgccgga cgagctaccc gccgtcaatt tcttgcgtga agaaaacgtc      60
tttgtgatga caacttctcg tgcgcctggt caggaaattc gtccacttaa ggttctgatc     120
cttaacctga tgccgaagaa gattgaaact gaaaatcagt ttctgcgcct gctttcaaac     180
tcacctttgc aggtcgatat tcagctgttg cgcatcgatt cccgtgaatc gcgcaacacg     240
cccgcagagc atctgaacaa cttctactgt aactttgaag atattcagga tcagaacttt     300
gacggtttga ttgtaactgg tgcgccgctg ggcctggtgg ggtttaatga tgtcgcttac     360
tggccgcaga tcaaacaggt gctggagtgg tcgaaagatc acgtcacctc gacgctgtct     420
gtctgctggg cggtacaggc cgcgctcaat atcctctacg gcattcctaa gcaaactcgc     480
accgaaaaac tctctggcgt ttacgagcat catattctcc atcctcatgc gcttctgacg     540
```

```
cgtggctttg atgattcatt cctggcaccg cattcgcgct atgctgactt tccggcagcg    600
ttgattcgtg attacaccga tctggaaatt ctggcagaga cggaagaagg ggatgcatat    660
ctgtttgcca gtaaagataa gcgcattgcc tttgtgacgg gccatcccga atatgatgcg    720
caaacgctgg cgcaggaatt tttccgcgat gtggaagccg gactagaccc ggatgtaccg    780
tataactatt tcccgcacaa tgatccgcaa aatacaccgc gagagagctg gcgtagtcac    840
ggtaatttac tgtttaccaa ctggctcaac tattacgtct accagatcgc gccatacgat    900
ctacggcaca tgtatccaac gctggattaa                                     930

<210> SEQ ID NO 28
<211> LENGTH: 9960
<212> TYPE: DNA
<213> ORGANISM: Artificial Sequence
<220> FEATURE:
<223> OTHER INFORMATION: pAscrSM

<400> SEQUENCE: 28
tgccgaacag ttctctatgc tctgcatata attcatctaa ggggacacct ttataaacac     60
cacttttaac aacagacact ccattaggat gcgcagaaat cgcccaatat tctcccgtcg    120
tttcactagg aatgtcataa ccaaattctt ttctgagccg attgccgccc cagattttt    180 tatgcatttg tgattgtaaa aacaaaggtt ctgccatagt gttctccttt ctgtttttca    240
atataccact atctagtttc agaggaaatc aagagtaatt atattcactt cattatcctc    300
ataaaatgaa aatttcgttc acgtaaattc taacagttta atattgaata ttagaaggtg    360
ctttaatctt ccaattcatt tttaattaac gcgctgctat cttttagct aaagcgagat    420 ttcccaatgt tgctgaacca ttttctgcaa cagctggtgt cacaatataa tctttaacat    480
ctggaactgg aagatagtca ttcaaaagtg aagtaaattt ttcacgaacc cgattgagca    540
tatgttcttg tgccataacg cctccgccaa atacaatgac ttgcggacga taaggacag    600 tcgcttgaat agccgcctga gcaatgtagt atgcctgaat atcccaaact ctgagttttt    660
gctcaattaa ctcaccacga ataccagtac gagcctctaa gctaggaccc gctgcaagtc    720
cttctaaaca gcctttatgg aaaggacagg tgcctacaaa accatgatga acatcattgg    780
gatgcggagc catgtaaacg tgtccagctt ccgtatgtcc cataccgcca atgaattcgc    840
cattttgaat agtccctgct ccaatgcctg ttccaatagt ataataaacc agacttttaa    900
catttgaacg agcaattgtt tccccataag cagaagaatt aacatctgtc gtaaagtaaa    960
atggaatttt aaaatcttta gaaattaagc cgacaaaatc aacgttagcc cagtttggct   1020
ttggtgttga agtaatgtaa ccataagtgt ctgaattttg atcaatatca atagggccaa   1080
aagaaccaat ggcaacactg gctaaatcag cttcaaattt tttaaagaaa gcaactgttt   1140
tttctattgt ttcataaggt gttgttgttg ggaactgaac ttttttctaaa atttgaaaat   1200 tttcatcacc tacagcacag acaaattttg ttccgccagc ttcgatgctg ccatataatt   1260
tagacataat aaacctctta tattttactt aacttaccaa atcaattttt ggatttgaat   1320
acccttaatc tacccttaag gactacttaa cattatatca taatttgcta aatttcaagt   1380
attagttagc caaaaggctt taatactatt gttactgaat cttttaagca gtcaaaaaga   1440
ccttacggtc tttctgataa tatttcttat tttttaactt caagtaagct atcacctaca   1500
gcaacagttc ctgaagaagc gagggtttca actgacgcat aatcggctgt attagtaaca   1560
atgaacattg ttgtattatc aagaccagct tctgcaattt tgtcactatc aaatgttccg   1620
agaacgtcac cttttttaat tttttgatct gcttgaactt tttgttcaaa tcctttacct   1680
```

```
tccattgata ctgtatcaat accaatatga ataagaatct ccgcaccatt gtctgactta   1740
ataccataag catggccagt atcaaaagca atttgaacag tcccatcaac cggtgcataa   1800
actgtattac cactaggttt gatagcaatc cccttaccca ttgcttcgct agaaaaaaca   1860
gggtcattaa cagaggttaa ttcaacagct tcaccagcaa gaggagccgc aagaacttca   1920
tcagtaactt gtgccttatt tgctgcagaa gcagcttctt ctggaatttc ttgcacttct   1980
tcaatagctt cttcgacagc agcttcagca gcaaagacat caacagcctt cgtcttacca   2040
tagccataag ttactgcaaa agctatagca aaactgatta attcacagac tacataaaat   2100
ggaatagaac ttgcccttaat agaaaggaaa ccaagaaaac ctgccgaacc aagggaaacc   2160
gctacaactt gaagtaagcc cgcaattgct gcagcactag ctgagccaat cagagcacaa   2220
aagaatggga aacgatattt caaattcacc ccaaaaagag caggttctgt aataccaaga   2280
agcgctgaca cacctgaaga agatgagaga cctttcatct tcttatcttt tgttaagaag   2340
taaattgcaa aggttgctgc gccttgtgcg acattggcca ttgaagctgt aacaaagata   2400
aagtcaccat gaccagtacc attttggaaa gctgaaatga gttgggtttc aatagctggg   2460
aaactttgat ggagaccagt cataactaca ggtgaataca gagcaccaaa gacacccata   2520
cctaggaatc ccgttgtatc atacagccat acgattccat ttgtaagcca gtcagaaact   2580
tctttcataa caggaccaat aacgataaat gtcaaaaatc cagtaataat aactgacaat   2640 aaggtgtaa aggtaaagtc aactgctgag ggcaatctct tatggaaaaa ttttttctaag   2700 atagataaaa gccatacagc cacaagtact ggaatcactt gataagtata acttgcctga   2760
gtaacatgca acccaaaaat attccaaaat cctgtataag caccaatagt agcagccttt   2820
gaaattggag cattagctgc taaaccaatg atatttgctg cccccggtgc gaccataatc   2880
atgccgattg aagctcctaa gaattggtta gcaccaaaac gtttagctgc tgaaatccca   2940
accaaaatgg gtaagaacca gaaggcgct gctgacatta ttgaatcat gtcagatgaa   3000 cccttaataa tcgggaattg ttgaaccagt gacttagtac caaataaacc ttctgaagtt   3060
aaaaagttat ttaaagccat taagagaccg cctgctacca aggcagggat aattggtaca   3120
aagatatcag acaacagttt gatcaaagcc ataataggat tgaactttt accactggca   3180 gcaatctttt tcaaatcatc tgttgagact tctgttaaac ctgtttgttt aataatttca   3240
tcataaacaa agttaacatc accagggcca ataataactt gatattgacc atccgtttta   3300
aaagttccct tgacatcagc attttttatcc aacgcttttt gatctacttt actgtcatct   3360
tttaaaacaa gacgaagacg tgtcgcacag tgagcggcag ctacaagatt atctttacca   3420
acagctgtga tgacttcact agctactttg ctataatcca tttgcaaaaa actccttaat   3480
aattattttg ttttgaaagc gttttttac tttccacgtt attcatttta tcattttttt   3540
ccaatatgtc aatcgtttta cataaaattc ttttttgcaa caaagattg attttagaa   3600 agaaaacgtt tactatatta gtatgtagat aaactattat taggagtaga taaacgatga   3660
atttgcctca aaatatcaga tatcgccgct atcaagattg gactgaagaa gaaataaaaa   3720
gtattaaaac caatgtagct ttgtctcctt ggcatacaac gtatcatata gaacctaaaa   3780
caggactcct taatgatcca aacgttttt cctattttaa tggaaaattt aacctttttt   3840
atcaaaattg gccatttgga gcagctcacg gcttaaaatc ttggatccat actgaaagtg   3900
aagacttagt ccatttcaaa gaaacaggta cagtcctta tcccgatact tcccatgaca   3960
gccatggtgc atactcgggc agtgcctatg aaatcggtga tcagcttttt ctcttttata   4020
```

-continued

```
caggaaatgt ccgagatgaa aattgggttc gtcatccact tcaaatcggc gcttttatgg    4080
ataaaaaagg taatatccaa aaatttactg atgtccttat taaacagcca aatgatgtta    4140
ctgaacactt tcgcgatccc caaattttta attataaagg acaattttac gctattgttg    4200
gagcacaaag tctagataaa aaaggattta tcaaactcta taaagctgtt gataatgata    4260
ttaagaattg gcaagaagtt ggtaatctag actttggcgg aagtaaatct gagtatatga    4320
ttgagtgccc aaatcttgtt tttataaacg aacagcctgt cctgatttat agtcctcagg    4380
gactcagtaa atctgaatta gattatcata atatttatcc taatacttac aaagtatgtc    4440
aatcgtttga cacagaaaag cctgccctag ttgatgcatc ggaaattcaa aatcttgact    4500
tcggatttga atgttatgct acccaagctt tcaatgctcc tgatggccgt gtttatgctg    4560
tctcatggat tgggttacca gatattgatt atccaagtga ttcatacgac tatcaaggag    4620
ctttgagcct cgtcaaagag ctaagcctaa aacacggtaa actctatcaa tatcccgttg    4680
aagctgttcg ttcattacgt tctgaaaaag aagcagtcac ttacaagcca gaaaccaata    4740
atacttatga attagagtta acttttgact cttcatcagt taatgaattg ctccttttg    4800
ctgataataa aggcaatggt ctagctatta cagttgatac taagatggga accattctga    4860
tcgatcgctc taaagcaggg gagcaatatg ccttagaatt tggaagccaa cgttcttgct    4920
ctatccaagc aaaagagact gttgtcaata ttttgttga caaatcgatt tttgaaattt    4980
ttattaataa gggagaaaaa gttttactg gacgtgtttt tccaaatgac aaacaaactg    5040
gtattgtgat taaatctgga aagccaagcg gtaattacta cgaattgaaa tattaactat    5100
ggttgcaaaa ttaacagatg tcgcaaaact cgctggcgta agtccaacaa ccgtttcacg    5160
cgtgattaat cgaaaaggct atctctctga aaaacaatt actaaagtac aggctgccat    5220
gaaaactcta ggatacaagc ccaataatct cgctcgcagc cttcagggga aatctgccaa    5280
gctaattgga cttatttccc ctaatatcag tcacatcttc tattctgaac ttattgaata    5340
tttagaaata gagttgttta acatggcta caaagccatt atttgtaaca gtcagaataa    5400
tcccgataaa gaacgggatt atctcgaaat gttagaagct aatcaggttg atggcattat    5460
ttccagtagt cacaacctcg gcattgatga ctatgagaaa gttctgctc ctattattgc    5520
ctttgatcgt aacttagcac ccaatattcc catcgtctct tctgacaatt ttgaaggcgg    5580
acgaatggcc gcaaaacttt taaaaaaaca cggctgccaa catcccatta tgatcgctgg    5640
aaaagataat tctaattctc ggacaggact gcgacaatta ggctttaagt ccgtctttgc    5700
tcaagcacct attttcatc tatctggaga gctgtccatc attcgtaaag aaatggaaat    5760
aaaagtaatt ctccaaaatg aaaaacctga tggtatcttt ttgtccgatg atatgacagc    5820
tatttttaaca atgaaaattg ctaaccagtt aaacattacc attccccatg aacttaaaat    5880
tattgggtac gatggaacac actttgttga gaactactat ccttatctaa caactattag    5940
gcaacctatt aaagatatcg cacatctttt ggtagacgta ttgctaaaga aaattgatca    6000
ccaagatact cctaaagatt atattctccc cgttggtctt tatcaggag aaagtgttta    6060
gaatcaaaag gtttatttag gtttgtcttt tgtgggttga ttaaaagtcc ttacctaatt    6120
aatgagcatc agttcaatgt caatatttaa tcaactttgc gcaaaagaat agacatacaa    6180
ttcttagttt taaattcaaa aagaagaggt aagatttaag cctaaaatct tacctcttct    6240
tttatcagcc cttattattt tctttcaagc acaaactgac ttaaaacgcc attaataaac    6300
ttactggatt tctcatctga atactttttt gcaatttcaa taatttcatt aagagcaaca    6360
cgttctggtg tttccttatg atatttaatt tcgtataaac ctaaacgcaa caggctctta    6420
```

```
tcaatcaaag tcaatcgaga aagcgtccag ccagactagt agggcaaact attaactggc      6480
gaactactta ctctagcttc ccggcaacaa ttaatagact ggatggaggc ggataaagtt      6540
gcaggaccac ttctgcgctc ggcccttccg gctggctggt ttattgctga taaatctgga      6600
gccggtgagc gtgggtctcg cggtatcatt gcagcactgg ggccagatgg taagccctcc      6660
cgtatcgtag ttatctacac gacggggagt caggcaacta tggatgaacg aaatagacag      6720
atcgctgaga taggtgcctc actgattaag cattggtaac tgtcagacca agtttactca      6780
tatatacttt agattgattt aaaacttcat ttttaattta aaaggatcta ggtgaagatc      6840 cttttgata atctcatgac caaaatccct taacgtgagt tttcgttcca ctgagcgtca      6900
gaccccttaa taagatgatc ttcttgagat cgttttggtc tgcgcgtaat ctcttgctct      6960
gaaaacgaaa aaaccgcctt gcagggcggt ttttcgaagg ttctctgagc taccaactct      7020
ttgaaccgag gtaactggct tggaggagcg cagtcaccaa aacttgtcct ttcagtttag      7080
ccttaaccgg cgcatgactt caagactaac tcctctaaat caattaccag tggctgctgc      7140
cagtggtgct tttgcatgtc tttccgggtt ggactcaaga cgatagttac cggataaggc      7200
gcagcggtcg gactgaacgg ggggttcgtg catacagtcc agcttggagc gaactgccta      7260
cccggaactg agtgtcaggc gtggaatgag acaaacgcgg ccataacagc ggaatgacac      7320
cggtaaaccg aaaggcagga acaggagagc gcacgaggga ccgccagggg gaaacgcct      7380 ggtatcttta tagtcctgtc gggtttcgcc accactgatt tgagcgtcag atttcgtgat      7440
gcttgtcagg ggggcggagc ctatggaaaa acggctttgc cgcggccctc tcacttccct      7500
gttaagtatc ttcctggcat cttccaggaa atctccgccc cgttcgtaag ccatttccgc      7560
tcgccgcagt cgaacgaccg agcgtagcga gtcagtgagc gaggaagcgg aatatatcct      7620
gtatcacata ttctgctgac gcaccggtgc agccttttt ctcctgccac atgaagcact      7680
tcactgacac cctcatcagt gccaacatag taagccagta tacactccgc tagcgctgag      7740
gtctgcctcg tgaagaaggt gttgctgact cataccaggc ctgaatcgcc ccatcatcca      7800
gccagaaagt gagggagcca cggttgatga gagctttgtt gtaggtggac cagttggtga      7860
ttttgaactt ttgctttgcc acggaacggt ctgcgttgtc gggaagatgc gtgatctgat      7920
ccttcaactc agcaaaagtt cgatttattc aacaaagcca cgttgtgtct caaaatctct      7980
gatgttacat tgcacaagat aaaaatatat catcatgaac aataaaactg tctgcttaca      8040
taaacagtaa tacaaggggt gttatgagcc atattcaacg ggaaacgtct tgctcgaggc      8100
cgcgattaaa ttccaacatg gatgctgatt tatatgggta taatgggct cgcgataatg      8160 tcgggcaatc aggtgcgaca atctatcgat tgtatgggaa gcccgatgcg ccagagttgt      8220
ttctgaaaca tggcaaaggt agcgttgcca atgatgttac agatgagatg gtcagactaa      8280
actggctgac ggaatttatg cctcttccga ccatcaagca ttttatccgt actcctgatg      8340
atgcatggtt actcaccact gcgatccccg ggaaaacagc attccaggta ttagaagaat      8400
atcctgattc aggtgaaaat attgttgatg cgctggcagt gttcctgcgc cggttgcatt      8460
cgattcctgt ttgtaattgt ccttttaaca gcgatcgcgt atttcgtctc gctcaggcgc      8520
aatcacgaat gaataacggt ttggttgatg cgagtgattt tgatgacgag cgtaatggct      8580
ggcctgttga acaagtctgg aaagaaatgc ataagctttt gccattctca ccggattcag      8640
tcgtcactca tggtgatttc tcacttgata accttatttt tgacgagggg aaattaatag      8700
gttgtattga tgttggacga gtcggaatcg cagaccgata ccaggatctt gccatcctat      8760
```

```
ggaactgcct cggtgagttt tctccttcat tacagaaacg gcttttcaa aaatatggta    8820 ttgataatcc tgatatgaat aaattgcagt ttcatttgat gctcgatgag tttttctaat    8880
cagaattggt taattggttg taacactggc agagcattac gctgacttga cgggacggcg    8940
gctttgttga ataaatcgaa cttttgctga gttgaaggat cagatcacgc atcttcccga    9000
caacgcagac cgttccgtgg caaagcaaaa gttcaaaatc accaactggt ccacctacaa    9060
caaagctctc atcaaccgtg gctccctcac tttctggctg gatgatgggg cgattcaggc    9120
ctggtatgag tcagcaacac cttcttcacg aggcagacct cagcgctcaa agatgcaggg    9180
gtaaaagcta accgcatctt taccgacaag gcatccggca gttcaacaga tcgggaaggg    9240
ctggatttgc tgaggatgaa ggtggaggaa ggtgatgtca ttctggtgaa gaagctcgac    9300
cgtcttggcc gcgacaccgc cgacatgatc caactgataa aagagtttga tgctcagggt    9360
gtagcggttc ggtttattga cgacgggatc agtaccgacg gtgatatggg gcaaatggtg    9420
gtcaccatcc tgtcggctgt ggcacaggct gaacgccgga ggatcctaga gcgcacgaat    9480
gagggccgac aggaagcaaa gctgaaagga atcaaatttg gccgcaggcg taccgtggac    9540
aggaacgtcg tgctgacgct tcatcagaag ggcactggtg caacggaaat tgctcatcag    9600
ctcagtattg cccgctccac ggtttataaa attcttgaag acgaaagggc ctcgtgatac    9660
gcctattttt ataggttaat gtcatgataa taatggtttc ttagacgtca ggtggcactt    9720
ttcggggaaa tgtgcgcgga acccctattt gtttatttt ctaaatacat tcaaatatgt    9780
atccgctcat gagacaataa ccctgataaa tgcttcaata atattgaaaa aggaagagta    9840
tgagtattca acatttccgt gtcgcccta ttcccttttt tgcggcattt tgccttcctg    9900
tttttgctca cccagaaacg ctggtgaaag taaaagatgc tgaagatcag ttgggtgcac    9960
```